United States Patent
Kim et al.

(10) Patent No.: US 10,537,603 B2
(45) Date of Patent: Jan. 21, 2020

(54) PHARMACEUTICAL COMPOSITION FOR PREVENTING OR TREATING ANGIOEDEMA, CONTAINING EXTRACT OF PEONY ROOT OR MIXTURE OF PEONY ROOT AND LICORICE AS ACTIVE INGREDIENT

(71) Applicant: Korea Institute of Oriental Medicine, Daejeon (KR)

(72) Inventors: Jin Sook Kim, Seoul (KR); Junghyun Kim, Daejeon (KR); Chan-Sik Kim, Daejeon (KR); Eunjin Shon, Daejeon (KR); Yun Mi Lee, Daejeon (KR); Young Sook Kim, Daejeon (KR); Sojin Choi, Daejeon (KR); Ik Soo Lee, Daejeon (KR); Dong Ho Jung, Daejeon (KR); Bo-Jeong Pyun, Daejeon (KR); Seung-Hyun Jung, Daejeon (KR)

(73) Assignee: Korea Institute of Oriental Medicine, Daejeon (KR)

( * ) Notice: Subject to any disclaimer, the term of this patent is extended or adjusted under 35 U.S.C. 154(b) by 348 days.

(21) Appl. No.: 15/313,654

(22) PCT Filed: May 21, 2015

(86) PCT No.: PCT/KR2015/005116
§ 371 (c)(1),
(2) Date: Nov. 23, 2016

(87) PCT Pub. No.: WO2015/178702
PCT Pub. Date: Nov. 26, 2015

(65) Prior Publication Data
US 2017/0209510 A1    Jul. 27, 2017

(30) Foreign Application Priority Data
May 23, 2014    (KR) ........................ 10-2014-0062201

(51) Int. Cl.
*A61K 36/65*    (2006.01)
*A61K 36/484*    (2006.01)

(52) U.S. Cl.
CPC ............ *A61K 36/65* (2013.01); *A61K 36/484* (2013.01); *A61K 2236/331* (2013.01); *A61K 2236/333* (2013.01); *A61K 2236/37* (2013.01)

(58) Field of Classification Search
None
See application file for complete search history.

(56) References Cited

FOREIGN PATENT DOCUMENTS

| CN | 1583111 | | 2/2005 |
| CN | 101204440 A | * | 6/2008 |
| JP | 2012-025777 | | 2/2012 |
| KR | 10-2004-0052213 | | 6/2004 |
| WO | WO 2015/178702 | | 11/2015 |

OTHER PUBLICATIONS

American Dragon. Ask the Doctor: Herb Formulas Shao Yao Gan Cao Tang. Internet archive date: Sep. 11, 2013. [Retrieved from the internet on: Jun. 2, 2019]. Retrieved from: <URL: https://web.archive.org/web/20130917094122/http://www.americandragon.com/Individualherbsupdate/BaiShao.html>. (Year: 2013).*
Castleman, M. "Licorice" from "The New Healing Herbs". Rodale. pp. 308-312 (Year: 2009).*
Clarke, J.H. Paeonia from "A Dictionary of Practical Materia Medica". London: The Homeopathic Publishing Company. pp. 707-710. (Year: 1902).*
Nairn, JG. "Solutions, Emulsions, Suspensions and Extractives" from Remington's Pharmaceutical Sciences. A. R. Gennaro, Ed. Mack Publishing Company: Pennsylvania. p. 1492. (Year: 1985).*
International Search Report dated Jul. 24, 2015 From the Korean Intellectual Property Office Re. Application No. PCT/KR2015/005116 and Its Translation Into English. (8 Pages).
Ahmad et al. "Medicinal Uses and Phytoconstituents of Paeonia Officinalis", International Research Journal of Pharmacy, 3(4): 85-87, 2012. Abstract, p. 86.
Liu et al. "Effects and Mechanisms of Chinese Herbal Medicine in Ameliorating Myocardial Ischemia-Reperfusion Injury", Evidence-Based Complementary and Alternative Medicine, 2013(Art.ID 925625): 1-14, Published Online Oct. 31, 2013.
Wu et al. "Survey of Current Experimental Studies of Effects of Traditional Chinese Medicine on Peripheral Nerve Regeneration", Chinese Journal of Integrative Medicine, 12(3): 229-233, Sep. 2006.

(Continued)

*Primary Examiner* — Amy L Clark

(57) ABSTRACT

The present invention relates to a pharmaceutical composition for preventing or treating angioedema, containing as an active ingredient a peony root extract or an extract of a mixture of peony root and licorice. In particular, the extract of a mixture of peony root and licorice according to the present invention inhibits the excessive generation of advanced glycation end products, which may cause macular degeneration, inhibits blood-retinal barrier breakdown causing retinal edema in various animal models, protects or treats a subretinal region causing dry macular degeneration, inhibits angiogenesis causing wet macular degeneration, and thus can be usefully used as an active ingredient for the composition for preventing and treating angioedema including macular degeneration, macular edema, retinal edema, or varicose veins.

14 Claims, 12 Drawing Sheets

(56) References Cited

OTHER PUBLICATIONS

Notification of Office Action dated Aug. 28, 2019 From the State Intellectual Property Office of the People's Republic of China Re. Application No. 201580026824.9 and Its Translation Into English. (16 Pages).
Li "Treatment of Central Chorioretinopathy Based on Liver and Spleen Theory", Ophthalmology Journal of Integrative Medicine, 1: 53-54, Dec. 1994.
Wu "Clinical Observation of Peony and Licorice Decoction in Treating 32 Cases of Muscle Pain Spasm Syndrome", Yunnan Journal of Traditional Chinese Medicine, 12(1): 20-22, Dec. 1991 & English Translation.

* cited by examiner

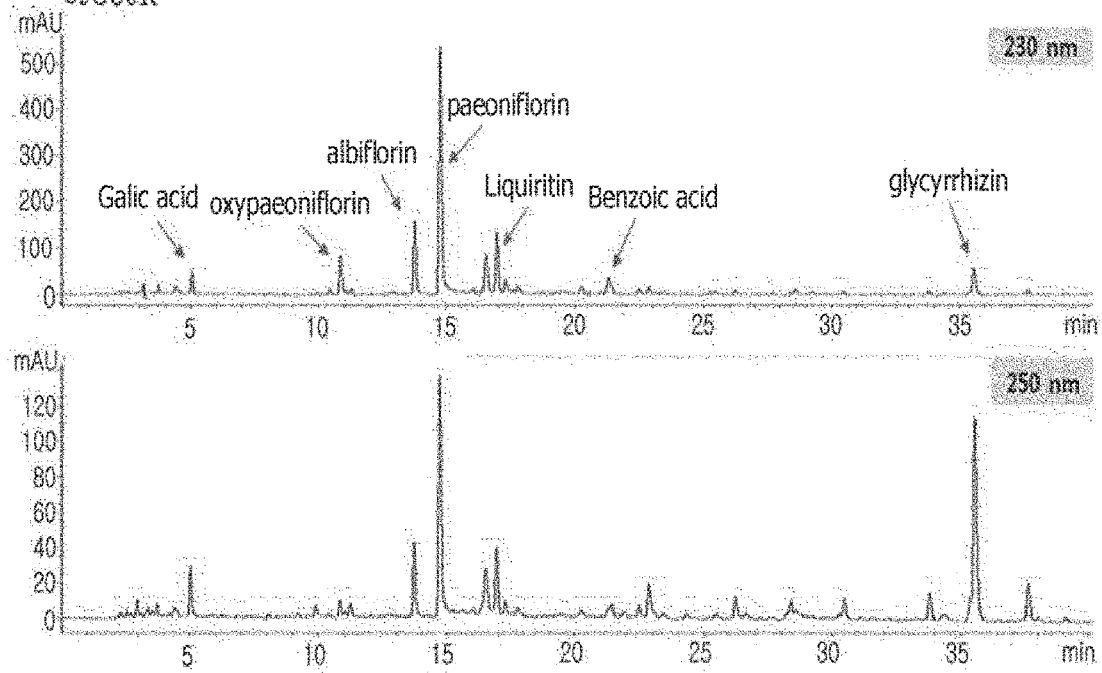
Fig. 1(a) CJG30R
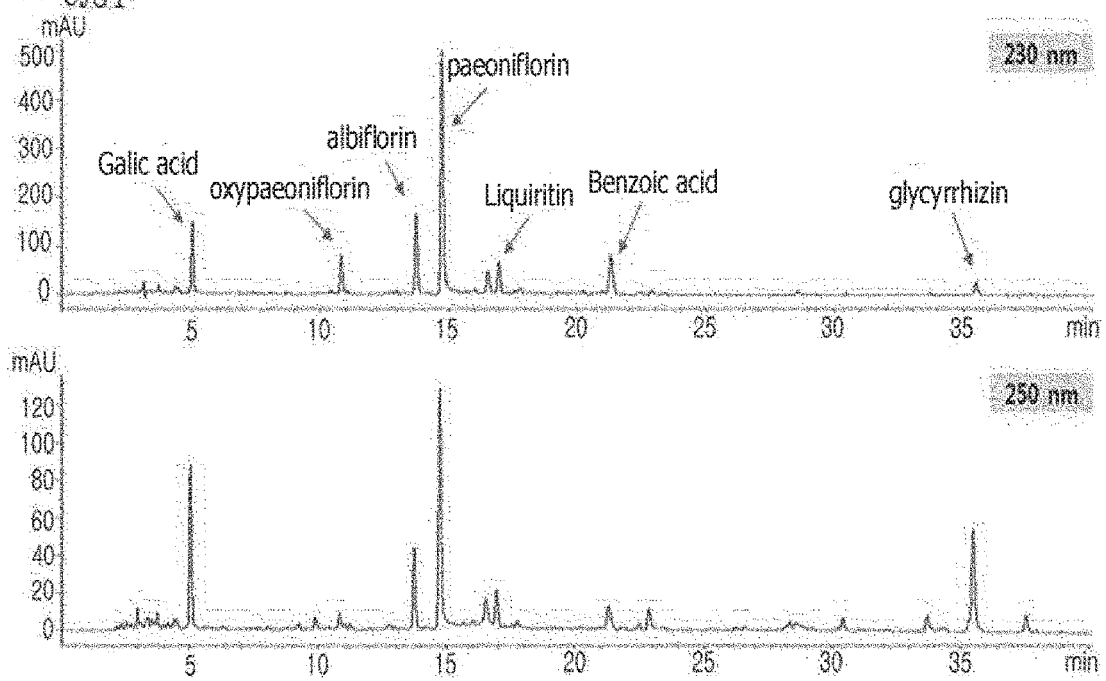
Fig. 1(b) CJGT (**p<0.01 vs CON; ##p<0.01 vs HG).

Fig. 6
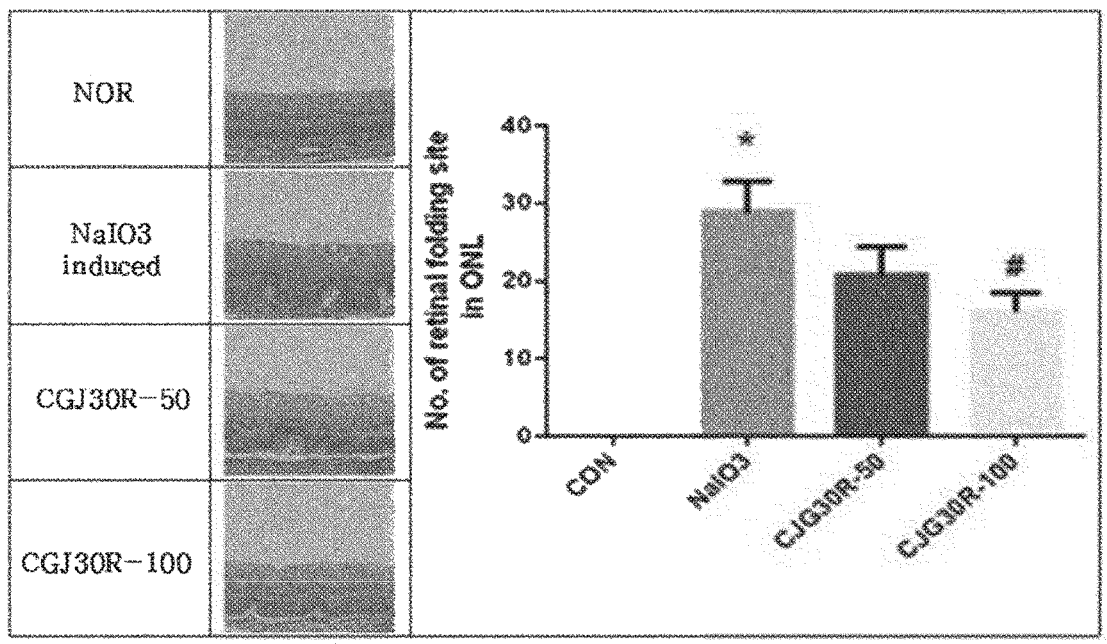
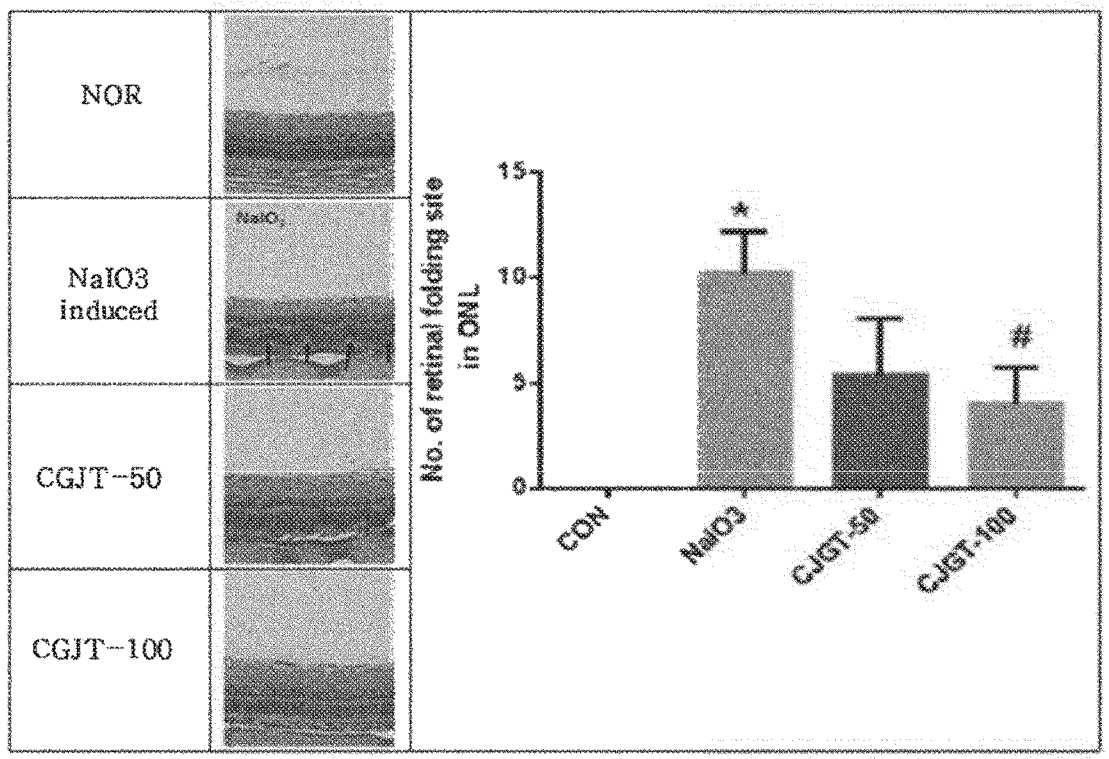

PHARMACEUTICAL COMPOSITION FOR PREVENTING OR TREATING ANGIOEDEMA, CONTAINING EXTRACT OF PEONY ROOT OR MIXTURE OF PEONY ROOT AND LICORICE AS ACTIVE INGREDIENT

RELATED APPLICATIONS

This application is a National Phase of PCT Patent Application No. PCT/KR2015/005116 having International filing date of May 21, 2015, which claims the benefit of priority of Korean Patent Application No. 10-2014-0062201 filed on May 23, 2014. The contents of the above applications are all incorporated by reference as if fully set forth herein in their entirety.

FIELD AND BACKGROUND OF THE INVENTION

The present invention relates to a composition for preventing or treating angioedema, such as retinal edema, macular degeneration, and varicose veins, containing an extract of peony root or a mixed extract of peony root and licorice as an active ingredient.

Angioedema is referred to as a disease that due to the increased permeability of blood vessels in the deepest recesses of skin or under skin, or beneath mucous membranes fluids flow out from the blood vessels and pool in surrounding tissues (i.e. edema is caused), and occurs well in relatively loose tissues, with being common around eyes or lips, or in hands and also occurring in tongues, mouths, larynges, mucous membranes such as gastrointestinal tract walls, and in particular blood-retinal barriers are damaged due to angioedema to cause macular edema, retinal edema or macular degeneration, or varicose veins.

Macular degeneration (age-related macular degeneration: AMD) is one of irreversible diseases, which is a representative ophthalmologic disease supervened to the elderly and leading to blindness. Due to population aging worldwide, the incidence is particularly increasing in developed countries. In the United States, macular degeneration is the main cause of blindness and also affected by environmental factors and genetic factors, and especially smoking was reported as the most deadly disease factors. Besides, obesity, and excessive intake of antioxidants and dietary fats also cause macular degeneration and influence to further progress. Therefore, healthy diet intake, weight control, moderate exercise, and no smoking reduce the onset of macular degeneration. The prevalence rate of early (dry) macular degeneration in the United States is about 3.9% in the 40-50 age groups, but 22.8% in the over 75 age groups, which showed to have very greater incidence rate (Beaver Dam Eye Study). Furthermore, it showed 5.4% of the incidence rate in the elderly group over 75 years, 7.1% of which were terminal macular degeneration patients. 1.9% of the Caucasian peoples living in Australia were terminal macular degeneration patients, with showing 0% of the incidence rate in the young age groups of 55 years or less but 18.5% in the elderly groups over 85 years for five years. Also, it was similar for Malay people in Asia (Blue Mountain Eye Study) (Progress in retinal and eye research, 1-15, 2014).

In the case of Korea, the Korean Retina Society reported that for the past year wet macular degeneration patients increased 7.4-fold and the incidence rate in 40, 50 middle-aged and senior adults increased 9-fold (2011). But most seriously, there is no macular degeneration therapeutic agent. Lucentis from Novartis, Switzerland, is an antibody therapeutic agent and very expensive, and it is impossible to stop the disease progression to such an extent as to restore sight.

Macular degeneration is classified as dry macular degeneration and wet macular degeneration. Dry macular degeneration is supervened due to the damaged macula by piling up drusen, which is a waste mass, on macula to damage metabolic connection between choroid and the upper part of macula and thus to damage macula. If this progress continues, it is advanced into wet macular degeneration. That is, since blood vessels function poorly by accumulating wastes in the macular region so that necessaries such as nutrients are not supplied, it starts to create new abnormal blood vessels (choroidal neovascularization: CNV). These generated vessels have very weak walls to leach proteins or red blood cells in the vessels into macular regions and retinas, whereby eventually due to vascular hemorrhage, various factors such as killing rod and cone photoreceptors and retinal pigment epithelial cells are developed to eventually lead to blindness (*Nutrition Research*, 34, 95-105, 2014; *Plos one*, 8, e71064, 2013).

Retinal pigment epithelial cells (RPEs) play an important role in maintaining healthy eyes by maintaining non-proliferative state and supporting Bruch's membrane (BrM). Cystatin C secreted from retinal pigment epithelial cells is a powerful cysteine protease inhibitors and plays an important role in normally controlling circulation of proteins in BrM, and the like. However, if advanced glycation end products are excessively accumulated, the expression and secretion of cystatin C proteins are lowered to cause an imbalance of proteolytic action in the RPE basal portion, so that the macular degeneration occurs (*IOVS*, 2014, 55 (2), 926-34). Therefore, when the production of the advanced glycation end products is inhibited, the macular degeneration may be also prevented (treated).

VEGF (Vascular Endothelial Growth Factor) is secreted from the retinal pigment epithelial cell layer to normally adjust the portion around Bruch's membrane (BrM) and to control growth and compactness of choroid capillary endothelial cells. Under normal conditions the VEGF secretion is very strictly regulated so as to prevent angiogenesis. However, if the VEGF secretion is not strictly regulated, this acts as a critical factor leading to the terminal stage of macular degeneration. If the VEGF secretion abnormally increases, then the abnormal and weak blood vessels which appear in macular degeneration are generated and destroyed (*J. Cell. Mol. Med.*, 17, 7, 833-843, 2013).

Retinal edema occurs, as the retinal capillary blood vessel walls are damaged in an abnormal environment to leach the proteins, red blood cells, and the like present in retinal capillary blood vessels into retinas, which pool in the retinas to cause an edema.

Varicose veins are a disease that veins appear out of skin, where the veins distributed in arms and legs are classified as large deep veins lying between muscles, superficial veins appearing underneath skin and perforating veins linking these two veins, mean among these that the superficial veins stretch and appear to be protruded out of skin, and are developed as the valves making blood flows inside the veins keep constant toward the heart always are damaged with vein walls being weak when the pressure in the varicose veins increases and thus the blood going to the heart is refluxed to stretch the veins.

Peony root is a perennial plant of Ranunculaceae with *Radix paeoniae alba* and *Radix paeoniae rubra. Radix paeoniae alba* and *Radix paeoniae rubra* are determined by the presence or absence of a shell, in which one having the shell is referred to as *Radix paeoniae rubra* and the other with striped shell to *Radix paeoniae alba* (*Altern. Med. Rev.* 6(5), 495-499, 2001). *Radix paeoniae alba* has, with *Radix paeoniae rubra*, an inhibitory effect of contraction against stomach and intestine smooth muscles, and uterine smooth muscles, a coronary arterial dilatation effect and effects of preventing atherosclerosis against vascular diseases, lowering blood pressure and improving blood flow. It appears that these effects of peony root extracts are derived from anti-oxidant effect (*J. Ethnopharmacol.* 67, 111-119, 1999), platelet anti-aggregating effect (*Planta Med*, 65, 595-599, 1999), antithrombotic effect (*Chem. Pharm. Bull,* 35 (2), 849-852, 1987), hyperlipidemia prevention (*Fitoterapia*, 75(1), 45-49, 2004), and the like. In addition, it has been reported that glycoside, some of components of peony root, is effective in treating cerebral infarction (*Zhong Yao Cai*, 23 (2), 95-97, 2000).

Licorice is one to dry roots and rhizomes of *Glycyrrhiza glabra* and *G. uralensis* and other congeneric plants, as an herbaceous perennial plant belonging to a legume family, and contains flavonoid-based compounds such as liquiritin, including glycyrrhizin of triterpen saponin, as main components. Pharmacological actions include adrenal cortical hormone-like actions, anti-gastric ulcer efficiencies, smooth muscle relaxation actions, liver protective effects, anti-inflammation, anti-allergic effects, antiviral effects (Oriental medicine pharmacology, Jipmoon Dang, 434-436, 2001).

In addition, the antibody (protein) medicines that are currently administrated partly adjust only the mechanism inhibiting neovascular vessels of many factors that cause macular degeneration or retinal edema. Furthermore, it is a well-known fact that they do not completely control this. It is not known for combined natural extract materials containing peony root extracts, or extracts of peony root and licorice which can overcome the limit of therapeutic agents that are currently administrated and control etiologies associated with retinal edema and macular degeneration at the same time.

Accordingly, the present inventors have exerted to develop combined natural extract materials for preventing and treating angioedema including retinal edema, macular degeneration and varicose veins, consequently found that peony root extracts, or mixed extracts of peony root and licorice inhibit generating advanced glycation end products, inhibit breakdown of blood-retinal barriers causing retinal edema in various animal models, protect or treat a sub-retinal region causing dry macular degeneration, and inhibit angiogenesis causing wet macular degeneration, so that the extracts may be usefully used as an active ingredient of the composition for preventing and treating angioedema including macular degeneration, macular edema, retinal edema or varicose veins, and completed the present invention.

SUMMARY OF THE INVENTION

It is an object of the present invention to provide a composition for preventing and treating angioedema containing a peony root extract, or a mixed extract of peony root and licorice as an active ingredient.

In order to achieve the above object, the present invention provides a pharmaceutical composition for preventing and treating angioedema containing a peony root extract, or a mixed extract of peony root and licorice as an active ingredient.

In addition, the present invention provides a health functional food for preventing and ameliorating angioedema containing a peony root extract, or a mixed extract of peony root and licorice as an active ingredient.

In addition, the present invention provides a method for treating angioedema comprising a step of administrating a pharmaceutically effective amount of a peony root extract, or a mixed extract of peony root and licorice to a subject suffering from angioedema.

In addition, the present invention provides a method for ameliorating angioedema comprising a step of administrating a pharmaceutically effective amount of a peony root extract, or a mixed extract of peony root and licorice to a subject suffering from angioedema.

In addition, the present invention provides a use of a peony root extract, or a mixed extract of peony root and licorice for use as a pharmaceutical composition for preventing and treating angioedema.

In addition, the present invention provides a use of a peony root extract, or a mixed extract of peony root and licorice for use as a health functional food for preventing and ameliorating angioedema.

The peony root extract, or the mixed extract of peony root and licorice according to the present invention inhibits the excessive generation of advanced glycation end products, inhibits breakdown of blood-retinal barriers causing retinal edema in various animal models, protects or treats a sub-retinal region causing dry macular degeneration, inhibits angiogenesis causing wet macular degeneration, and thus can be usefully used as an active ingredient for the composition for preventing and treating angioedema including macular degeneration, macular edema, retinal edema or varicose veins.

BRIEF DESCRIPTION OF THE SEVERAL VIEWS OF THE DRAWINGS

FIGS. 1(a) and 1(b) are diagrams showing chromatograms of the mixed extract of peony root and licorice (CJG30R (a) and CJGT (b)) measured by HPLC (liquid high performance chromatography).

NOR: C57BL/6 normal mice;
MNU: MNU-induced macular degeneration animal models;
CJGT-50: MNU-induced macular degeneration animal models+CJGT 50 mg/kg/day administration group; and
CJGT-100: MNU-induced macular degeneration animal models+CJGT 100 mg/kg/day administration group.

FIG. 6 is a diagram determining a preventive effect of macular degeneration through damage prevention of retinal pigment epithelial cells in NaIO$_3$ animal models:
NOR: C57BL/6 normal mice;
NaIO3: NaIO$_3$ induced animal models;
CJG30R-50: NaIO$_3$ induced animal models+CJG30R 50 mg/kg/day administration group;
CJG30R-100: NaIO$_3$ induced animal models+CJG30R 100 mg/kg/day administration group;
CJGT-50: NaIO$_3$ induced animal models+CJGT 50 mg/kg/day administration group; and
CJGT-100: NaIO$_3$ induced animal models+CJGT 100 mg/kg/day administration group.

Figure 7:
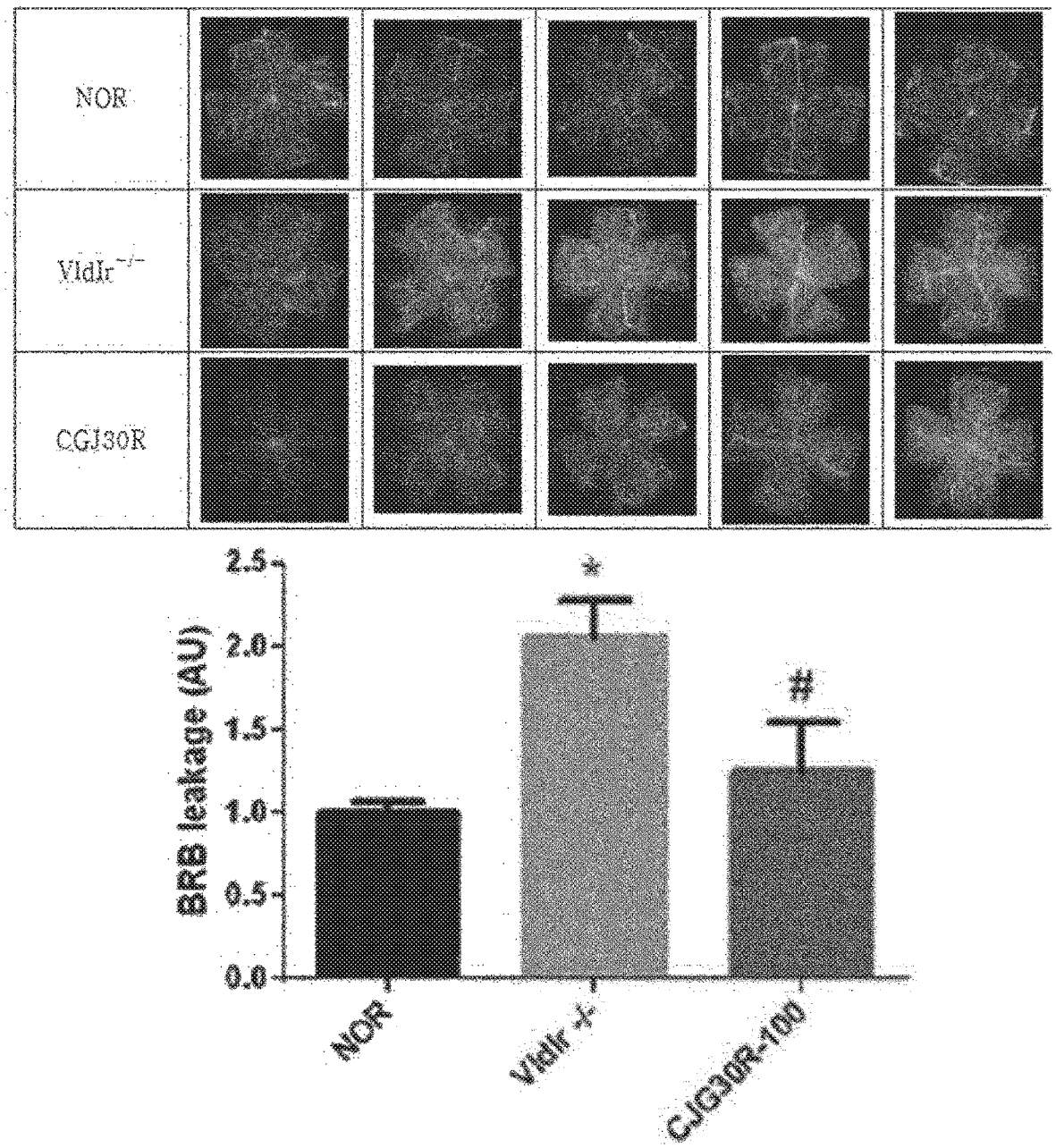

FIG. 7 is a diagram determining an inhibitory effect of retinal blood vessel damage in Vldlr$^{-/-}$ macular degeneration animal models:
NOR: C57BL/6 normal mice;
Vldlr$^{-/-}$: wet macular degeneration mice; and
CJG30R-100: Vldlr$^{-/-}$ induced animal models+CJG30R 100 mg/kg/day administration group.

Figure 8:
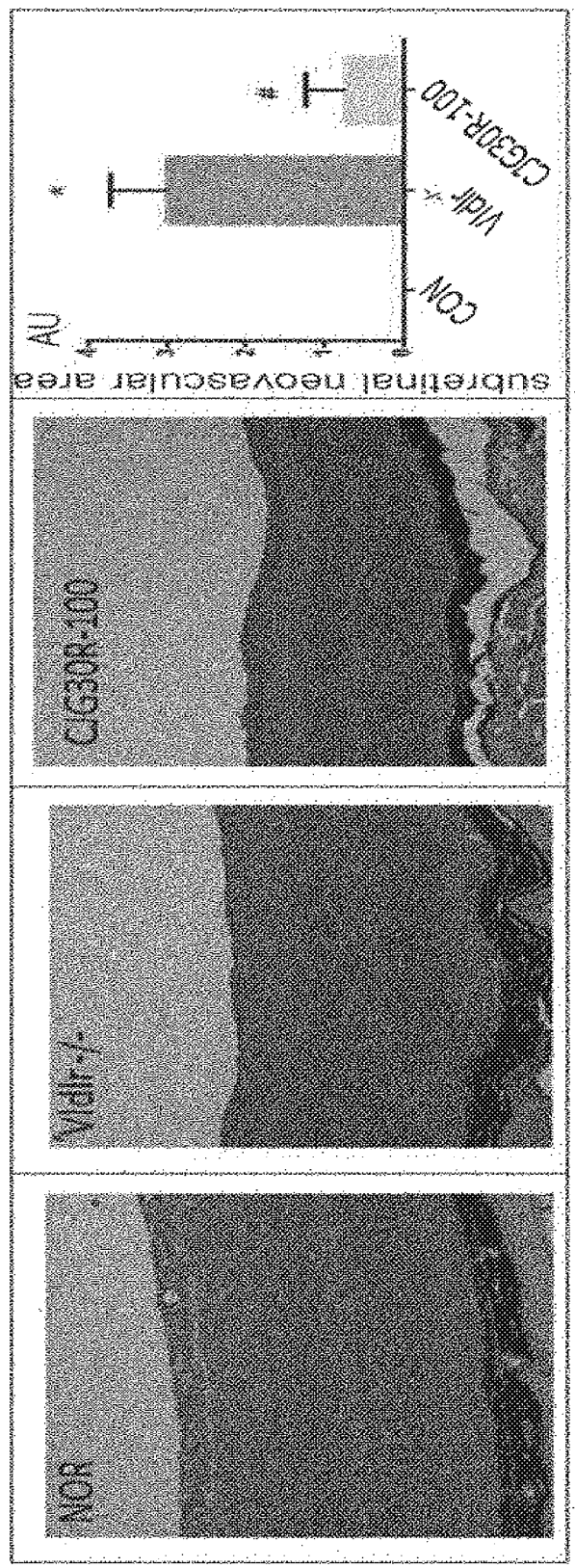

FIG. 8 is a diagram determining an inhibitory effect of retinal neovascular vessel generation in Vldlr$^{-/-}$ macular degeneration animal models:
NOR: C57BL/6 normal mice;
Vldlr$^{-/-}$: wet macular degeneration mice; and
CJG30R-100: Vldlr$^{-/-}$ mice+CJG30R 100 mg/kg/day administration group.

Figure 9:
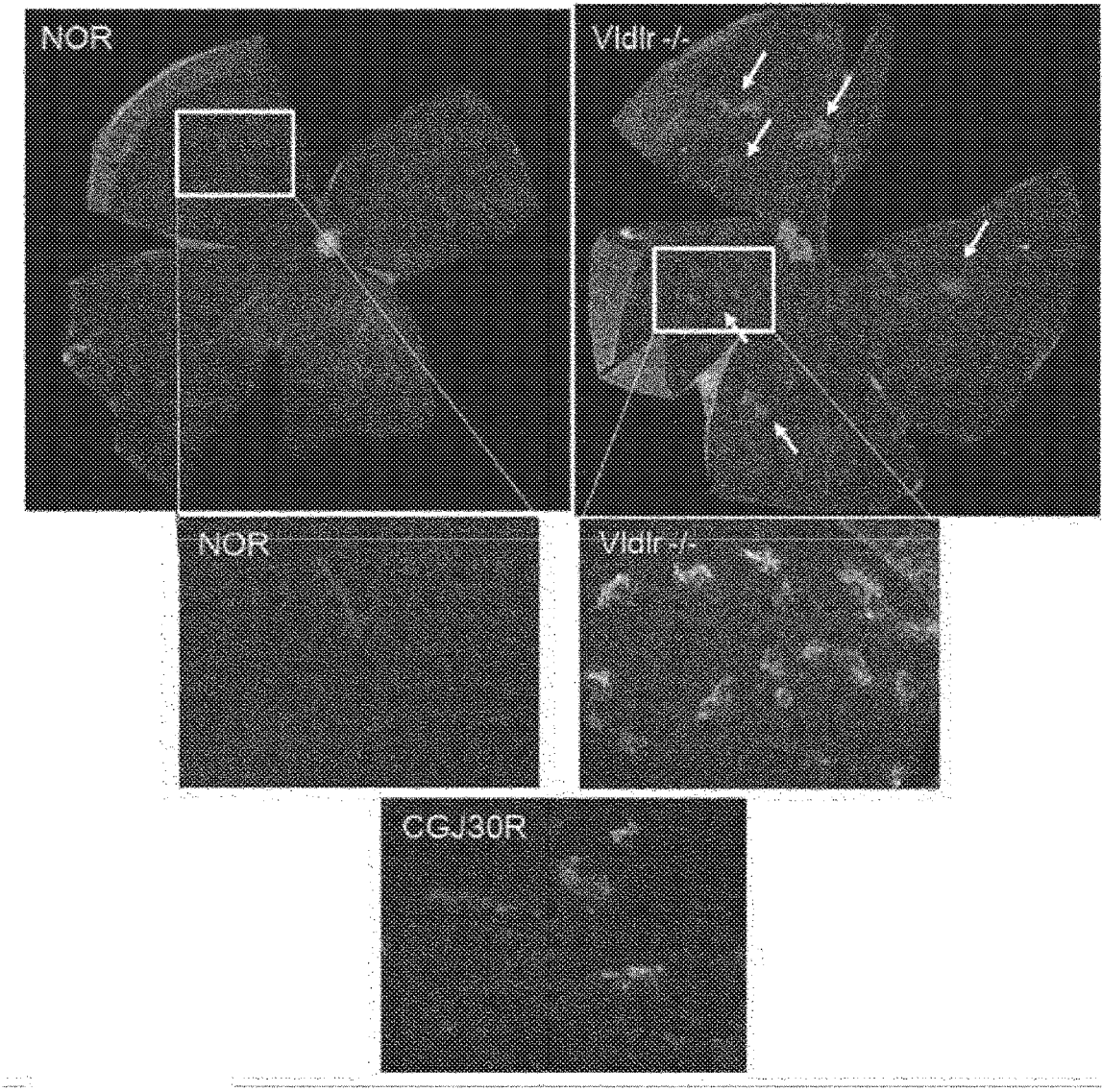

FIG. 9 is a diagram determining an inhibitory effect of pigment epithelial cell damage in Vldlr$^{-/-}$ macular degeneration animal models:
NOR: C57BL/6 normal mice;
Vldlr$^{-/-}$: wet macular degeneration mice; and
CJG30R-100: Vldlr$^{-/-}$ mice+CJG30R 100 mg/kg/day administration group.

Figure 10:
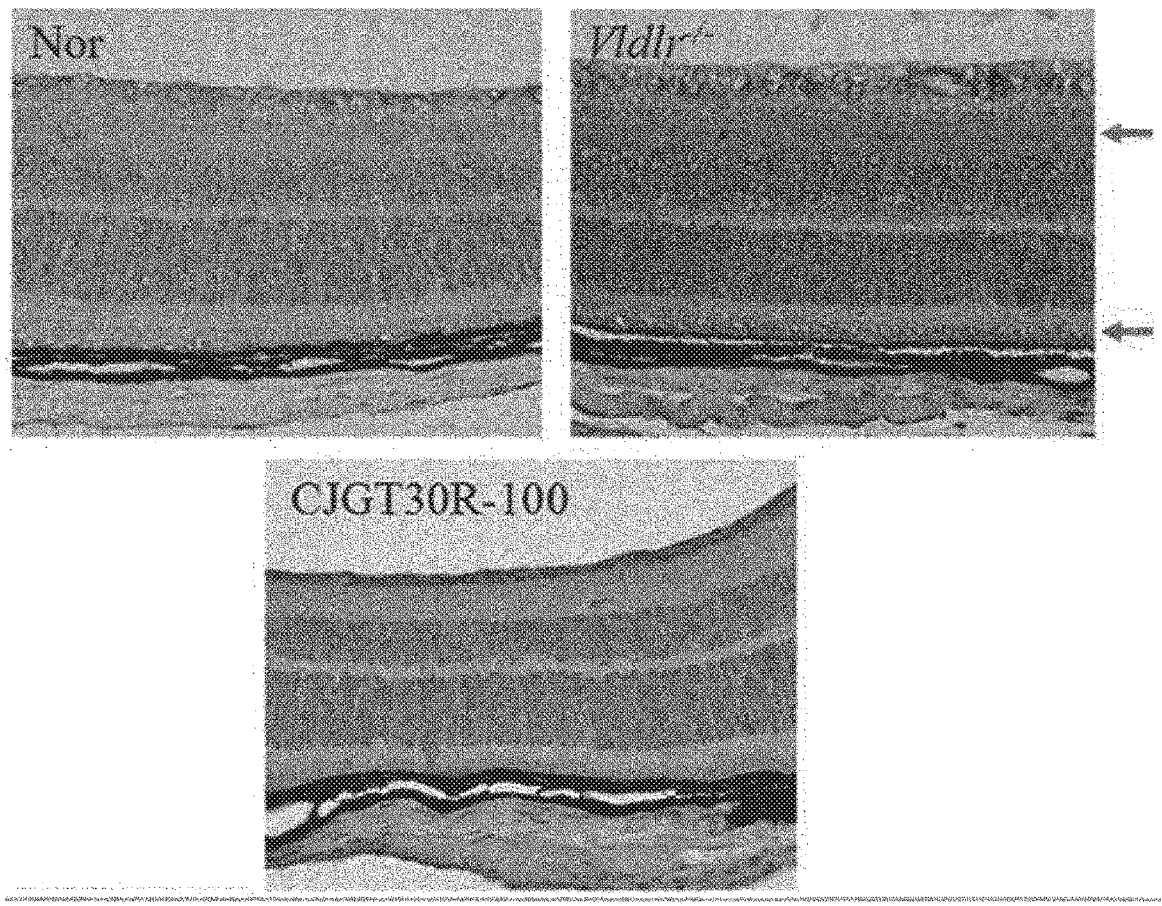

FIG. 10 is a diagram determining an inhibitory effect of VEGF expression (dark purple staining: indicated by arrows) in retinas of Vldlr$^{-/-}$ mice:
Nor: C57BL/6 normal mice;
Vldlr$^{-/-}$: wet macular degeneration mice; and
CJG30R-100: Vldlr$^{-/-}$ mice+CJG30R 100 mg/kg/day administration group.

Figure 11:
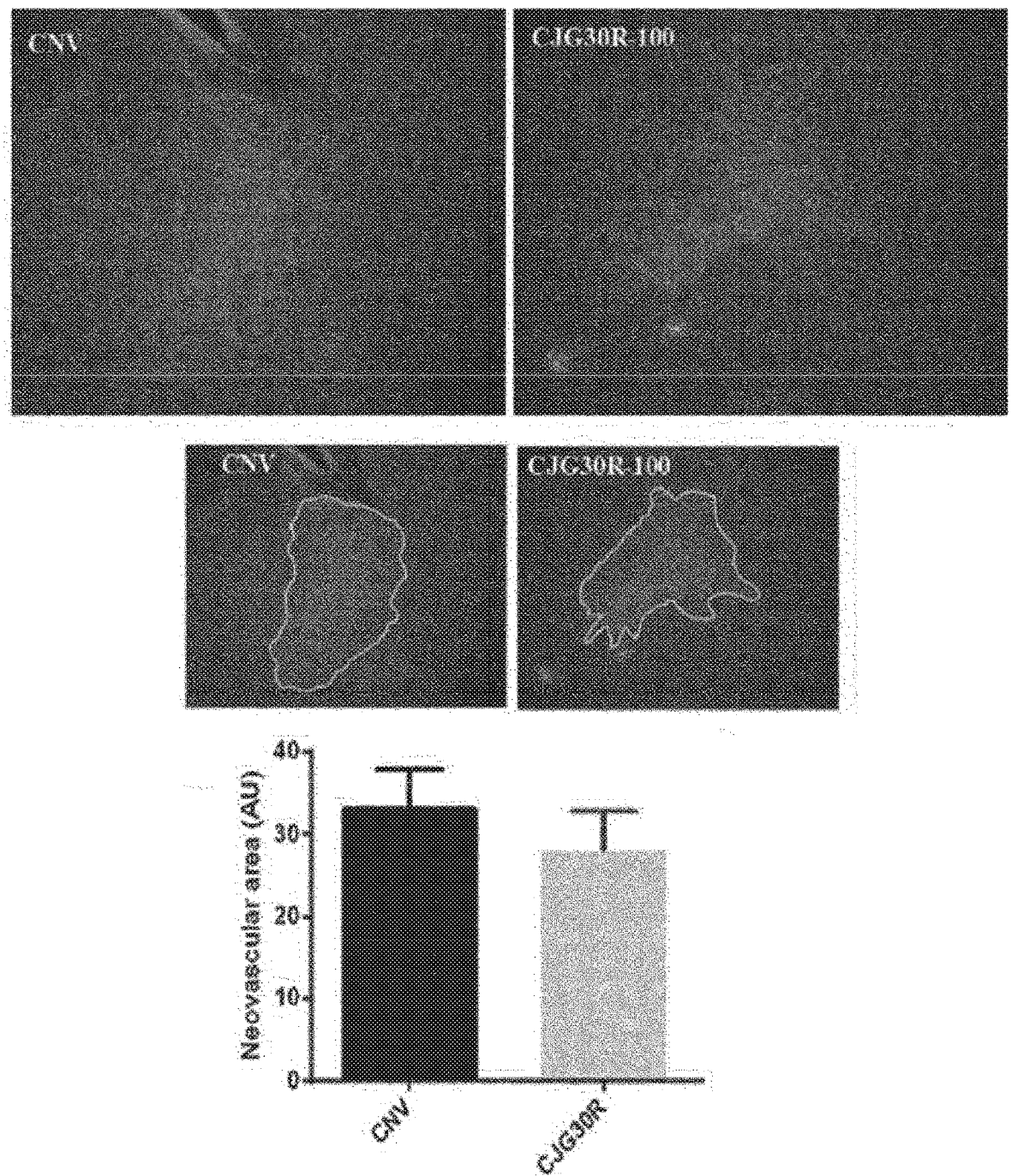

FIG. 11 is a diagram determining an inhibitory effect of retinal neovascular vessel generation of CJG30R in laser-induced choroidal neovascularization (CNV) rat models:
CNV: wet macular degeneration mouse models treated with laser; and
CJG30R: wet macular degeneration mouse models treated with laser+CJG30R 100 mg/kg/day administration group.

Figure 12:
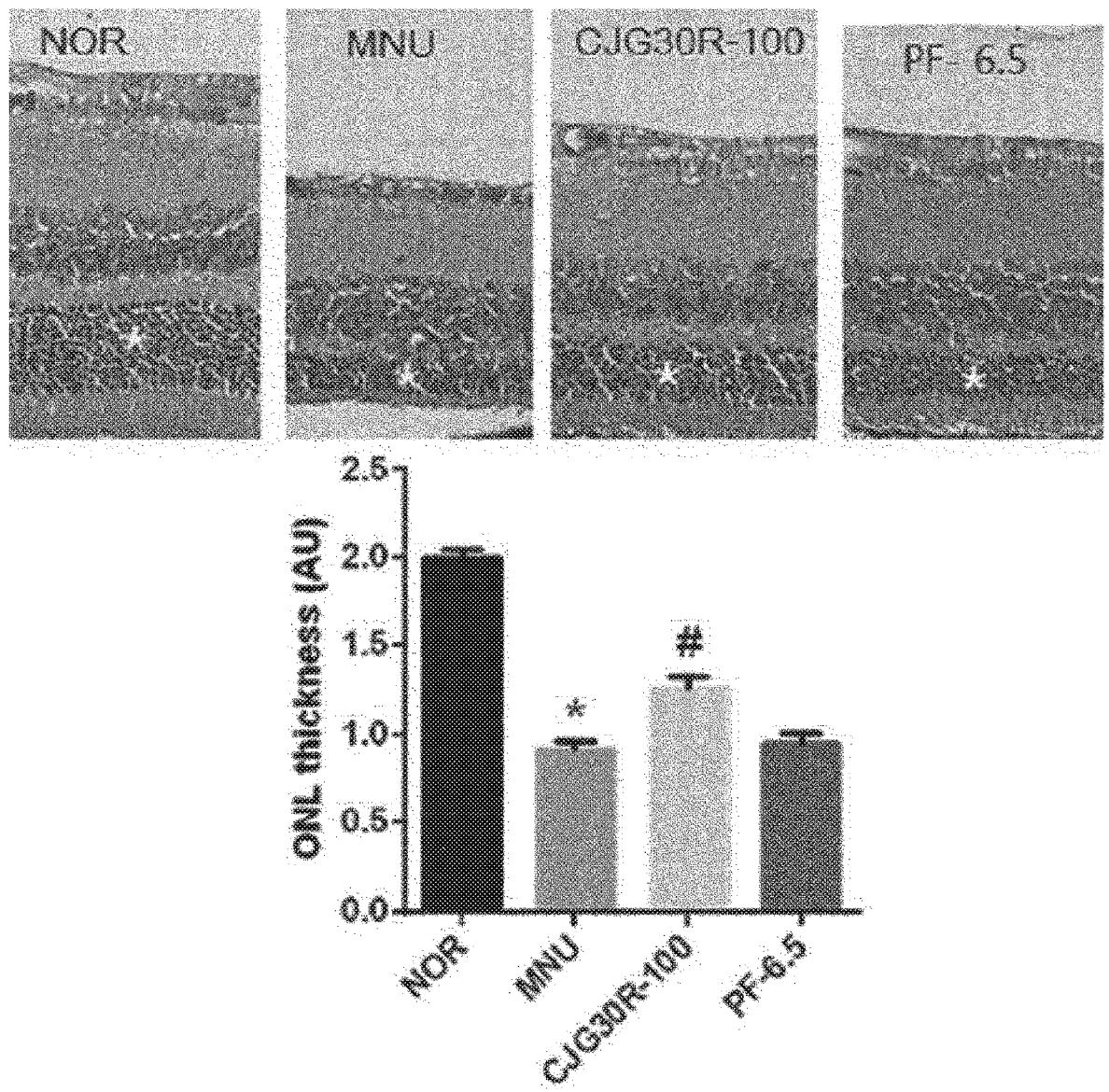

FIG. 12 is a diagram comparing and analyzing prevention and treatment of macular degeneration of CJG30R and paeoniflorin (PF) in MNU-induced age-related macular degeneration rodent animal models:
NOR: C57BL/6 normal mice;
MNU: N-methyl-N-nitrosourea (MNU)-induced animal models;
CJG30R-100: MNU-induced animal models+CJG30R 100 mg/kg/day administration group; and
PF-6.5: MNU-induced animal models+paeoniflorin (PF) 6.5 kg/day administration group.

DESCRIPTION OF SPECIFIC EMBODIMENTS OF THE INVENTION

Hereinafter, the present invention will be described in detail.

The present invention provides a pharmaceutical composition for preventing and treating angioedema containing a peony root extract, or a mixed extract of peony root and licorice as an active ingredient.

Said peony root extract, or mixed extract of peony root and licorice exhibits effects to inhibit the excessive generation of advanced glycation end products, to inhibit breakdown of blood-retinal barriers causing retinal edema in various animal models, to protect or treat a sub-retinal region causing dry macular degeneration, and to inhibit angiogenesis causing wet macular degeneration.

In addition, said angioedema is preferably any one selected from the group consisting of macular degeneration, macular edema, retinal edema and varicose veins, but is not limited thereto.

Said peony root extract, or mixed extract of peony root and licorice is preferably prepared by a process for preparing comprising the following steps, without being limited thereto:

1) a step of extracting by adding an extraction solvent to peony root, or peony root and licorice;
2) a step of filtering the extract of step 1); and
3) a step of drying the filtered extract of step 2) after concentrating it under reduced pressure.

In the process, as the peony root and licorice in step 1), those cultivated or those that are commercially available may be used without limitation. As said peony root, both *Radix paeoniae alba* and *Radix paeoniae rubra* are available.

Said peony and licorice are mixed preferably in a weight ratio of 10:1 to 1:1, more preferably in a weight ratio of 10:1, 8:1 and 4:1, and most preferably in a weight ratio of 2:1.

As the extraction solvent, water, alcohol or a mixture thereof is preferably used. As said alcohol, $C_1$ to $C_2$ lower alcohol is preferably used, and as the lower alcohol, 30% ethanol, 50% ethanol, 70% ethanol or methanol is preferably used. Preferably, the extraction method includes reduced pressure and high temperature extraction, boiling water extraction, reflux extraction, hot water extraction, cold extraction, normal temperature extraction, ultrasonic extraction or vapor extraction, but is not limited thereto. It is preferred to add the extraction solvent 1 to 10 times the amount of peony root and licorice for extraction. The extraction temperature is preferably 30 to 100° C., but is not limited thereto. In addition, the extraction time is preferably 2 to 48 hours, but is not limited thereto. Moreover, the number of times of extraction is preferably 2 to 5 times, but is not limited thereto.

In the process, the concentration under reduced pressure of step 3) utilizes vacuum decompressive concentrator or vacuum rotary evaporator, without being limited thereto. In addition, drying includes preferably reduced pressure drying, vacuum drying, effervescent drying, spray drying or lyophilization, but is not limited thereto.

Figure 2:
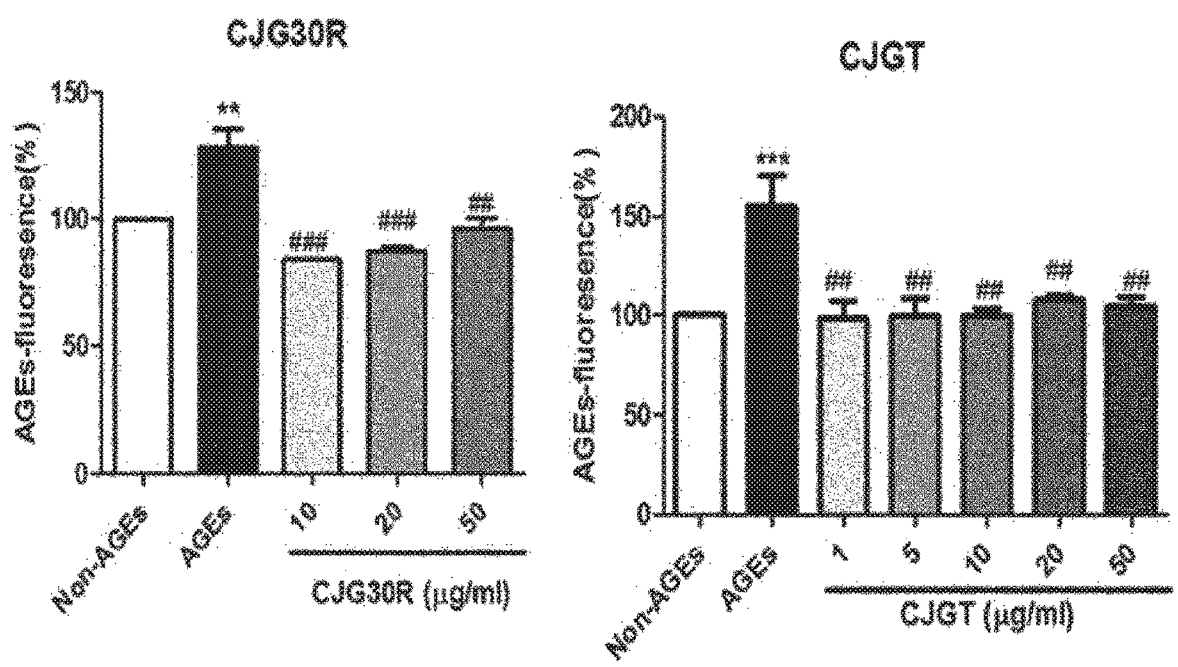
FIG. 2 is a diagram determining an inhibitory effect of advanced glycation end product generation in ECM (Extracellular Matrix) treated with glycolaldehyde.
Figure 3:
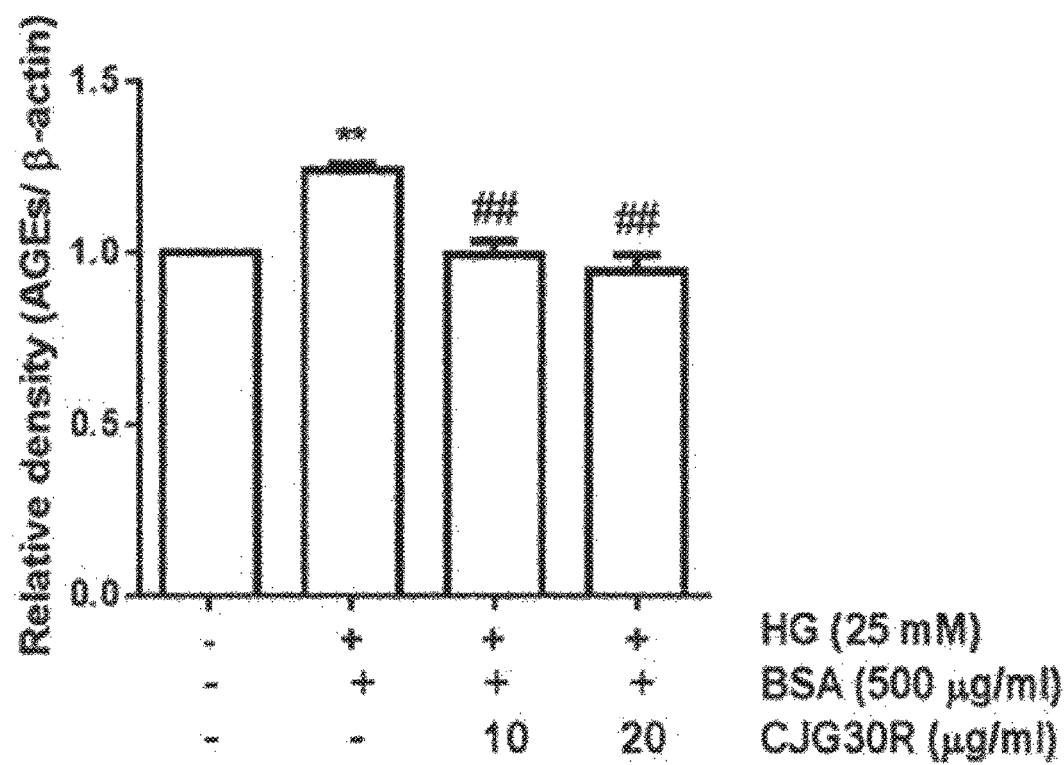
FIG. 3 is a diagram determining an inhibitory effect of advanced glycation end product generation of the mixed extract of peony root and licorice (CJG30R) in human retinal pigment epithelial cell lines under a hyperglycemic environment.

In specific examples of the present invention, the present inventors have prepared the peony root extract, or the mixed extract of peony root and licorice using hot water and ethanol and then determined the inhibitory effect of advanced glycation end product generation, and consequently, found that the peony root extract, or the mixed extract of peony root and licorice of the present invention exhibited the inhibitory effect of advanced glycation end product generation more remarkable than the positive control group and in particular had very excellent inhibitory effect of advanced glycation end product generation, considering that aminoguanidine as the positive control group is a synthesized single compound (see Table 2, FIG. 2 and FIG. 3). In addition, it was confirmed that by verifying the fact that the extract inhibits breakdown of blood-retinal barriers causing retinal edema in various animal models, protects or treats a sub-retinal region causing dry macular degeneration, and inhibits angiogenesis causing wet macular degeneration, it may be usefully used as an active ingredient of the composition for preventing and treating angioedema (FIG. 2 to FIG. 6).

The composition containing the extract or the mixed extract of the present invention may comprise one or more active ingredients showing the same or similar functions in addition to the above ingredient.

The compositions of the present invention may further comprise a pharmaceutically acceptable additive whereas the pharmaceutically acceptable additive, starch, gelatinized starch, microcrystalline cellulose, milk sugar, povidone, colloidal silicon dioxide, calcium hydrogen phosphate, lactose, mannitol, taffy, gum arabic, pregelatinized starch, corn starch, powder cellulose, hydroxypropyl cellulose, Opadry, sodium starch glycolate, carnauba wax, synthetic aluminum silicate, stearic acid, magnesium stearate, aluminum stearate, calcium stearate, sucrose and the like may be used. The pharmaceutically acceptable additive according to the present invention is preferably included in 0.1 to 90 parts by weight relative to said composition, but is not limited thereto.

That is, the composition of the present invention may be administrated in various oral or parenteral dosage forms when clinically administered in practice, and compounded using diluents or excipients, such as general fillers, extenders, binders, wetting agents, disintegrants, and surfactants active agents when formulated. A solid preparation for oral administration includes tablets, pills, powders, granules, capsules, and the like, and such a solid preparation may be compounded by mixing the mixed extract with at least one or more excipients, for example, starch, calcium carbonate, sucrose, lactose or gelatin, etc. Furthermore, in addition to simple excipients, lubricants such as magnesium stearate and talc may also be used. A liquid preparation for oral administration includes suspensions, internal solutions, emulsions and syrups, where various excipients, for example, wetting agents, sweeteners, aromatics and preservatives may be included other than water or liquid paraffin as simple diluents. Formulations for parenteral administration may include sterile aqueous solutions, non-aqueous solvents, suspensions, emulsions, lyophilized formulations, and suppositories. In non-aqueous solvents and solvents for suspending, propylene glycol, polyethylene glycol, vegetable oils such as olive oil, injectable esters such as ethyl oleate, and the like may be used. As base materials of suppositories, witepsol, macrogol, tween 61, cacao butter, sevum laurin, glycerogelatin and the like, may be used.

The composition of the present invention may be orally administered or parenterally administered according to the desired method, and it is preferred to select skin external use or an injection method of intraperitoneal injection, intrarectal injection, subcutaneous injection, intravenous injection, intramuscular injection or intrathoracic injection. The dosage has various ranges depending on body weight, age, gender, health condition, diet, administration time, administration method, excretion rate, and disease severity of a patient.

The dosage of the composition of the present invention has various ranges depending on body weight, age, gender, health condition, diet, administration time, administration method, excretion rate, and disease severity of a patient, where the daily dose may be 0.0001 to 100 mg/kg, preferably 0.001 to 10 mg/kg, based on the amount of the extract or the mixed extract of the present invention, and may be administered 1-6 times per day.

The composition of the present invention may be used alone, or in combination with surgery, radiation therapy, hormone therapy, chemical therapy, and methods of using biological response modifiers, for preventing and treating angioedema.

In addition, the present invention provides a health functional food for preventing and ameliorating angioedema containing a peony root extract, or a mixed extract of peony root and licorice as an active ingredient.

The mixed extract is prepared after mixing said peony root and licorice, preferably in a weight ratio of 10:1 to 1:1, more preferably in a weight ratio of 10:1, 8:1 and 4:1 and most preferably in a weight ratio of 2:1, without being limited thereto.

The angioedema is preferably any one selected from the group consisting of macular degeneration (edema), retinal edema and varicose veins, but is not limited thereto.

Said peony root extract, or mixed extract of peony root and licorice inhibits generating advanced glycation end products (Table 2, FIG. 2 and FIG. 3), inhibits breakdown of blood-retinal barriers causing retinal edema in various animal models, protects or treats a sub-retinal region causing dry macular degeneration, and inhibits angiogenesis causing wet macular degeneration, and thus exhibits anti-angioedema effects, so that the extracts may be usefully used as an active ingredient of the composition for preventing and treating angioedema (FIG. 4 to FIG. 10).

Hereinafter, the present invention will be described in detail by Examples and Experimental Examples.

However, the following Examples and Experimental Examples are merely to illustrate the present invention in detail, by which the content of the present invention is not restricted.

<Example 1> Preparation of Mixed Extract of Peony Root and Licorice, and Peony Root Extract To prepare mixed extracts of peony root and licorice, peony root and licorice were purchased and used on Baekje Dang (Daejeon, Korea) in March 2013, and stored at a cold chamber of diabetic complications research team in Korea Institute of Oriental Medicine (Daejeon, Korea).

<1-1> Preparation of 30% Ethanol Extract of Peony Root and Licorice

A mixed extract (CJG30R) of peony root and licorice in 30% ethanol was prepared by mixing 6 g of peony root and 3 g of licorice (2:1), adding a total of 9 g to 54 ml of 30% ethanol and repeatedly extracting to reflux twice the mixture at 50° C. for 3 hours.

<1-2> Preparation of 50% Ethanol Extract of Peony Root and Licorice

A mixed extract (CJG50R) of peony root and licorice in 50% ethanol was prepared in the same manner as Example <1-1> above by mixing 6 g of peony root and 3 g of licorice (2:1), adding a total of 9 g to 54 ml of 50% ethanol and repeatedly extracting to reflux twice the mixture at 50° C. for 3 hours.

<1-3> Preparation of 70% Ethanol Extract of Peony Root and Licorice

A mixed extract (CJG70R) of peony root and licorice in 70% ethanol was prepared in the same manner as Example <1-1> above by mixing 6 g of peony root and 3 g of licorice (2:1), adding a total of 9 g to 54 ml of 70% ethanol and repeatedly extracting to reflux twice the mixture at 50° C. for 3 hours. Yield was 23.5%.

<1-4> Preparation of Hot Water Extract of Peony Root and Licorice

To prepare a hot water extract of peony root and licorice, 6 g of peony root and 3 g of licorice (2:1) were mixed, distilled water of 10 times was added to a total of 9 g, and then the mixture was shaken by high-speed vacuum cold concentration extractor or a decocting device for about 2 hours to be concentrated under reduced pressure, and dried to prepare the hot water extract of peony root and licorice (CJGT).

<1-5> Preparation of Peony Root Extract

To prepare a hot water extract of peony root, distilled water of about 6 times was added to peony root, shaken by a decocting device for about 2 hours to be concentrated under reduced pressure, and dried to prepare the hot water extract of peony root (CJ).

<Example 2> Analysis of Indicator Components in Mixed Extracts of Peony Root and Licorice (CJG30R and CJGT) Through HPLC To analyze indicator components in mixed extracts of peony root and licorice (CJG30R and CJGT), each 10 microliters was taken from CJG30R and CJGT, injected into the column and subjected to HPLC (high performance liquid chromatography) to obtain chromatograms.

The used HPLC system was equipped with 1200 HPLC, DAD detector and Chemstation software from Agilent, and Luna 5C-18 (4.0×250 mm) analytical column from Phenomenex Inc. Samples were injected using a sample automatic injector, a mobile phase using a mixed solution of water and methanol had a flow rate of 1.0 ml/min, and wavelengths were set at 230 and 250 nm. A gradient started from water:methanol (70:30) and after 35 minutes had to be water:methanol (0:100), with being eluted by 100% methanol for 10 minutes. All the used analyzing solvents were HPLC grade solvents (Fisher scientific).

As a result, as shown in Table 1 and FIGS. 1(a) and 1(b), it was confirmed that the indicator components of CJG30R and CJGT are gallic acid, oxypaeoniflorin, albiflorin, paeoniflorin, liquiritin, benzoic acid, glycyrrhizin (FIGS. 1(a) and 1(b))).

TABLE 1

Content of paeoniflorin in CJG30R and CJGT through HPLC analysis

| | Content of paeoniflorin (%) |
|---|---|
| CJG30R | 6.5 |
| CJGT | 6.1 |

<Experimental Example 1> Determination of Inhibitory Effect on Advanced Glycation End Product (AGE) Generation To determine the inhibitory effect of advanced glycation end product generation of the peony root extract, or the mixed extract of peony root and licorice, the present inventors used 10 mg/ml of bovine serum albumin (Sigma, St. Louis, Mo., USA) dissolved in 50 mM phosphate buffer (pH 7.4) as a protein source and a mixed liquid of 0.2 M fructose and 0.2 M glucose as a sugar source, respectively.

The extracts of <Example 1> and a positive control group (aminoguanidine) were dissolved in 30 μl of 0.2% DMSO, and then again dissolved in 15% tween 80. The protein source, the sugar source and the extracts of the present invention as prepared above were mixed and compounded to a total of 1 ml, and then each cultured at 37° C. for 7 days to allow for glycation. At this time 0.02% azide (sodium azide) was added thereto to prevent from generating bacteria during the culture period. After the culture fluorescence (spectrofluorometric detector; Bio-TEK, Synergy HT, USA; Ex: 350 nm; Em: 450 nm) was measured and then calculated with Equation 1 below, with showing the result in Table 2.

[Equation 1]

$$\text{Generation inhibition ratio } (\%) = \left\{ 100 - \frac{(FS \text{ of sample group}) - (FS \text{ of sample blank test group})}{(FS \text{ of control group}) - (FS \text{ of control blank test group})} \right\} \times 100$$

(FS is fluorescence strength)

As a result, as shown in Table 2 below, it was confirmed that the inhibitory effect of advanced glycation end product generation in the hot water extracts of peony root and licorice was 1.2 times superior as compared to aminoguanidine (AG) of the positive control group. It was also confirmed that the effect in the 30%, 50% and 70% ethanol extracts of peony root and licorice was 1.7 times to 2.3 times superior, respectively, as compared to the positive control group and the effect in the peony root extract of Example <1-5> was 12 times superior (Table 2).

Therefore, considering that aminoguanidine as the positive control group is the synthesized single compound, it was confirmed that the mixed extracts of the present invention have a very excellent inhibitory effect of advanced glycation end product generation.

TABLE 2

| Sample | $IC_{50}$ (μg/ml) |
|---|---|
| Extract of Example <1-1> (CJG30R) | 46.77 ± 0.88 |
| Extract of Example <1-2> (CJG50R) | 41.66 ± 1.22 |
| Extract of Example <1-3> (CJG70R) | 35.26 ± 1.16 |

TABLE 2-continued

| Sample | IC$_{50}$ (μg/ml) |
| --- | --- |
| Extract of Example <1-4> (CJGT) | 69.44 ± 1.66 |
| Extract of Example <1-5> (CJ) | 6.84 ± 0.09 |
| Aminoguanidine (AG: positive control group) | 81.38 ± 2.70 |

<Experimental Example 2> Inhibitory Effect on Advanced Glycation End Product Generation in ECM Treated with Glycolaldehyde After treating with glycolaldehyde, the inhibitory effect of advanced glycation end product generation in CJG30R and CJGT prepared in <Example 1> above, was confirmed.

Extracellular matrices (ECMs, Sigma-Aldrich, cat. no. c-3867) were dispensed by 10 μg/cm², and then coated at 4° C. overnight. The next day, ECMs of the coated plate were removed, completely dried at room temperature, and then subjected to be a total amount of 100 μl, together with 100 mM glycolaldehyde (Sigma-Aldrich) and CJG30R and CJGT, having pre-diluted varying concentrations (1, 5, 10, 20, 50 μg/ml), and reacted at 37° C. for 4 hours, whereby it was confirmed whether to inhibit generation of advanced glycation end products (AGEs). In the positive control group, the generation of AGEs was confirmed by adding only 100 mM glycolaldehyde (Sigma-Aldrich). The resultants were washed with PBS twice, and then 100 μl of 50 mM sodium borohydride (Sigma-Aldrich) was added thereto to neutralize the remaining aldehyde groups for 5 minutes. After the neutralization, the resultants were washed with PBS twice, and confirmed with a fluorescence analyzer (Ex. 370 nm/Em 440 nm), while again adding 100 μl of PBS. In statistical processing, the value of p<0.05 or more was a significant value using Prism 5.0 program (GraphPad).

As a result, as shown in FIG. 2, it was confirmed that CJG30R CJGT significantly inhibited the advanced glycation end product generation in a concentration-dependent manner ( p<0.01 vs Non-AGEs; * p<0.001 vs Non-GEs; ## p<0.01 vs AGEs; ### p<0.001 vs AGEs: FIG. 2).

<Experimental Example 3> Determination of Inhibitory Effect of CJG30R on Advanced Glycation End Product Generation in Human Retinal Pigment Epithelial Cell Lines Under Hyperglycemic Environment It was confirmed that the CJG30R prepared in <Example 1> above represented the inhibitory effect of advanced glycation end product generation in human retinal pigment epithelial cell lines under a hyperglycemic environment.

Specifically, human retinal pigment epithelial cell lines (ARPE-19: ATCC No. CRL-2302) under a hyperglycemic environment were cultured in 5% CO$_2$ incubator with Dulbecco's Modified Eagle Medium (DMEM, Gibco, USA). After culturing at a final concentration of BSA of 500 μg/ml and in a hyperglycemic condition of 25 mM, CJG30R of the present invention was treated in concentrations (10, 20 μg/ml). In addition, the positive control group was treated with aminoguanidine (AG, 10 mM). Samples were washed with 1×PBS, treated with Laemmli Sample Buffer (cat. no. 161-0737, Bio-Rad Laboratories, CA, USA), boiled at 100° C. for 5 minutes, quantified for proteins with BCA (Pierce Biotechnology, IL, USA), and then used. After electrophoresis (120 V, 2 hours) of proteins in 10% polyacrylamide gel (PAGE) containing SDS, the proteins were transferred into a PVDF membrane (Bio-Rad Laboratories, CA, USA) with a transfer buffer (0.25 M Tris, 1.92 M glycine, pH 8.3-8.4) (250 mA, 1.5). After blocking TBS-T (200 mM Tris, 1.37 M NaCl, 0.05% Tween 20) solution with 5% non fat milk, AGE antibodies (Anti-AGEs monoclonal Ab, Clone No. 6D12) were reacted at 4° C. After washing, HRP-conjugated secondary antibodies were reacted, again washed, and then reacted with enhanced chemiluminescence (ECL), analyzed with LAS-3000 (Fuji film, JPN), and statistically processed with GraphPad Prism 5 (San Diego).

As a result, as shown in FIG. 3, it was confirmed that CJG30R of the present invention concentration-dependently (10 μg/ml, 20 μg/ml) inhibited the advanced glycation end product generation even in human retinal epithelial cells under a hyperglycemic environment (## P<0.01 vs HG) (FIG. 3).

<Experimental Example 4> Determination of Cross-Linking Breaking Ability of Advanced Glycation End Products The fragmentation effect of cross-linking of matrix proteins with advanced glycation end products in the mixed extracts (CJG30R, CJGT) prepared in <Example 1> above was confirmed. The used positive control group was ALT-711 (Alteon Inc., Ramsey, N.J.).

Specifically, 1.0 μg AGE-BSA (Transgenic Inc., Kobe, Japan) was dispensed into a collagen-coated 96-well microtiter plate (Greiner Bio-One, Germany), and then cultured at 37° C. for 4 hours to cross-link AGE-BSA and collagen. After removing the unbound AGE-BSA by washing 0.05% PBST three times, the mixed extracts and ALT-711 are added thereto and cultured at 37° C. for 4 hours. Then, the resultants were washed with 0.05% PBST, and to detect the remaining AGE-BSA cross-linked with collagen, mouse monoclonal anti-AGE-BSA antibodies (6D12, Transgenic Inc., Kobe, Japan) were diluted in 1:250, dispensed, and then cultured at 37° C. for 1 hour. After 1 hour, the resultants were washed with 0.05% PBST, and HRP-linked goat anti-mouse IgG antibodies (SantaCruz, USA) were reacted to stain TMB (3,3',5,5-tetramethylbenzidine) with matrices, and then absorbance was measured at 450 nm. The fragmentation effect (%) of cross-linking of AGE-BSA was calculated as Equation 2 below.

[Equation 2]

$$\text{Fragmentation effect (\%)} = \frac{\text{Absosrbance of well with added drug}}{\text{Absosrbance of well without added drug}} \times 100$$

As a result, as shown in Table 2, it was confirmed that the cross-linking breaking ability of advanced glycation end products in the hot water extracts of peony root and licorice were 2198 times superior as compared to ALT-711 of the positive control group, the effect in the 30%, 50% and 70% ethanol extracts of peony root and licorice was 53.5 times, 66.8 times, and 72.9 times, respectively, and the effect in the peony root extract was also 16891 times as compared to ALT-711 of the positive control group (Table 3).

TABLE 3

| Sample | IC$_{50}$ (μg/ml) | Effect relative to ALT-711 (positive control group) |
|---|---|---|
| Extract of Example <1-1> (CJG30R) | 319.07 ± 17.07 | ×53.5 |
| Extract of Example <1-2> (CJG50R) | 255.48 ± 17.11 | ×66.8 |
| Extract of Example <1-3> (CJG70R) | 233.87 ± 20.36 | ×72.9 |
| Extract of Example <1-4> (CJGT) | 7.76 ± 5.66 | ×2198 |
| Extract of Example <1-5> (CJ) | 1.01 ± 0.19 | ×16891 |
| ALT-711 (positive control group) | 17,060 ± 2.35 | — |

In conclusion, it was confirmed that the inventive materials inhibited generation of advanced glycation end products, inhibited generation of advanced glycation end products in the ECM coated with glycolaldehyde, also broke cross-linking of matrix proteins with the already generated advanced glycation end products, and significantly inhibited generation of advanced glycation end products in human retinal pigment epithelial cell lines under a hyperglycemic environment.

<Experimental Example 5> Determination of Inhibitory Effect of Retinal Edema Caused by Breakdown of Blood-Retinal Barriers in Animal Models <5-1> Laboratory Animal Breeding and Experimental Design As the laboratory animals 7-week-old male SD rats after birth were adapted and then used. Feed and drinking water were free fed. To induce breakdown of blood-retinal barriers, rat VEGF proteins (vascular endothelial growth factor, R & D research, USA) were administrated into the left eye and the control group or the CJGT of the present invention was injected into the right eye. The rats were anesthetized 24 hours after drug administration and 50 mg/ml fluorescein-dextran was injected into the left ventricle. After 10 minutes, eyes were enucleated and retinas were separated. The separated retinas were mounted with an aqueous mounting medium, and then observed and analyzed. For quantitative analysis, blood was drawn after injecting 50 mg/ml fluorescein-dextran into the left ventricle, and eyes were enucleated and retinas were separated after removing the remaining fluorescein-dextran in the blood vessels at a rate of 60 ml/min. The weight of the separated retina was measured and the fluorescence of the supernatant after centrifugation was measured with an ELISA reader.

<5-2> Experimental Results

Figure 4:
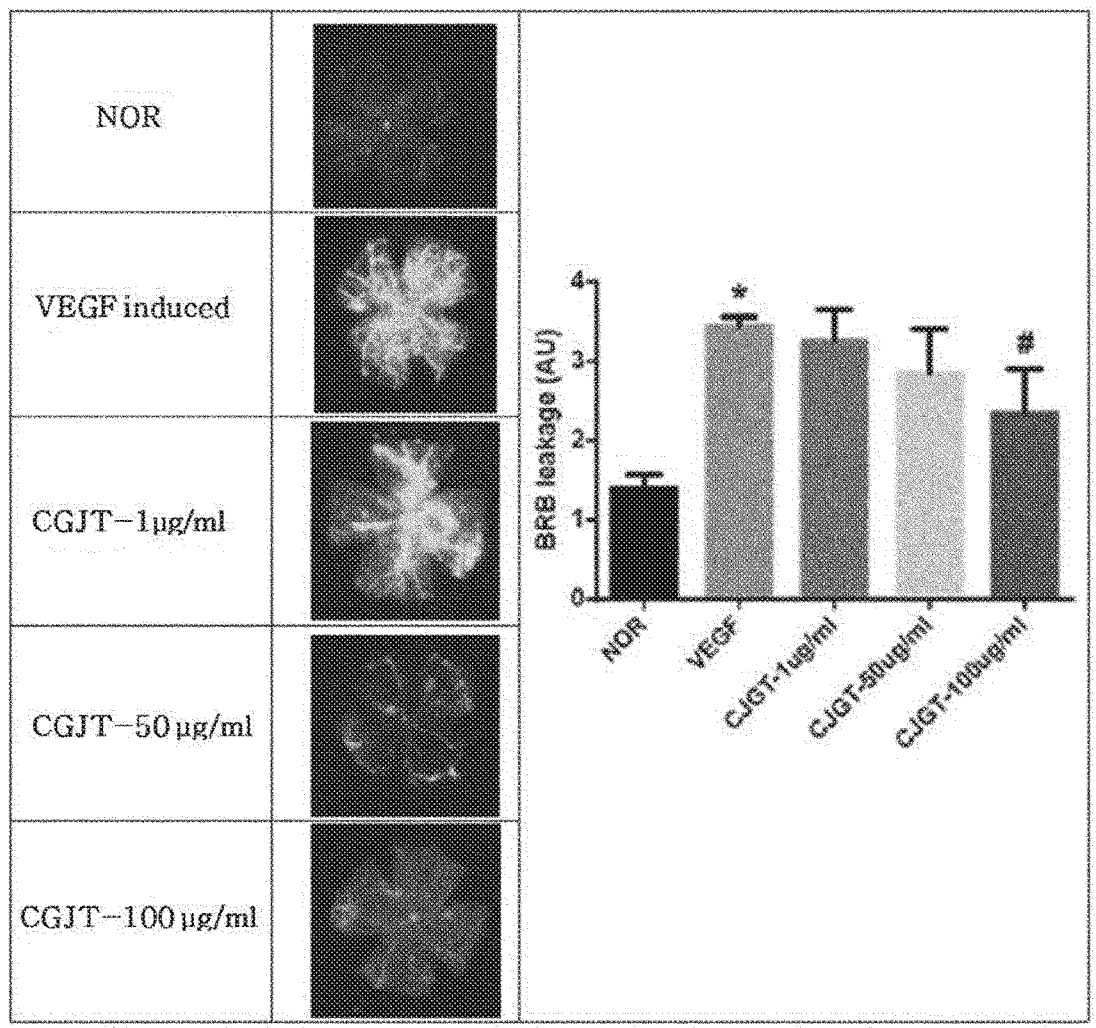
FIG. 4 is a diagram determining an inhibitory effect of the breakdown of blood-retinal barriers causing retinal edema in animal models:
  Nor: normal control group;
  VEGF: VEGF (vascular endothelial growth factor) treatment group;
  CJGT-1 µg/ml: a treatment group with 1 µg/ml of hot water extract of peony root and licorice of the present invention;
  CJGT-50 µg/ml: a treatment group with 50 µg/ml of hot water extract of peony root and licorice of the present invention; and
  CJGT-100 µg/ml: a treatment group with 100 µg/ml of hot water extract of peony root and licorice of the present invention.

As shown in FIG. 4, it was confirmed that in the normal group no leakage remark of fluorescence was observed, but in all the individuals of VEFG administration group the fluorescent materials were significantly (P<0.05) effused out of the blood vessels due to blood-retinal barrier damage (the more the blood-retinal barriers are damaged, the more brightly it appears). However, in the group administrating 100 μg/ml of CJGT prepared in <Example 1> above the effect of angioedema due to inhibition of blood-retinal barrier damage was confirmed by significantly (P<0.05) inhibiting the leakage phenomenon of fluorescent materials from the blood vessels by VEFG (FIG. 4).

<Experimental Example 6> Determination of Preventive and Therapeutic Effect in MNU-Induced Age-Related Macular Degeneration <6-1> Laboratory Animal Breeding and Experimental Design The 6-week-old male C57BL/6 mice were used after acclimatization for 1 week. To induce damage and degeneration of photoreceptor cells among morphological changes of retinal tissues appearing in macular degeneration, 1% (0.05% acetic acid) N-methyl-N-nitrosourea (MNU, Sigma, USA) was intraperitoneally injected to the 7-week-old male C57BL/6 mice (60 mg/kg). The same amount of 0.05% acetic acid was intraperitoneally administered to the normal group. Test drugs were suspended and compounded in 0.5% sodium carboxymethyl cellulose (CMC), orally administrated once in a concentration of 50 mg/kg and 100 mg/kg one day before MNU administration, and orally administrated once per day for 7 days after MNU administration. The same amount of 0.5% CMC only was orally administrated to the MNU-induced group and the normal group.

After completing administration of the test drugs, eyes were enucleated by carrying out an autopsy on the mice, and then mounted on 10% neutralized formalin for one day and embedded in paraffin to prepare slide sections. Slide sections were stained with Hematoxylin & Eosin (H & E) and observed under an optical microscope. The damage and degeneration of the photoreceptor cells were measured and evaluated by thickness changes in the outer nuclear layer of the retinal tissues.

<6-2> Experimental Results

Figure 5:
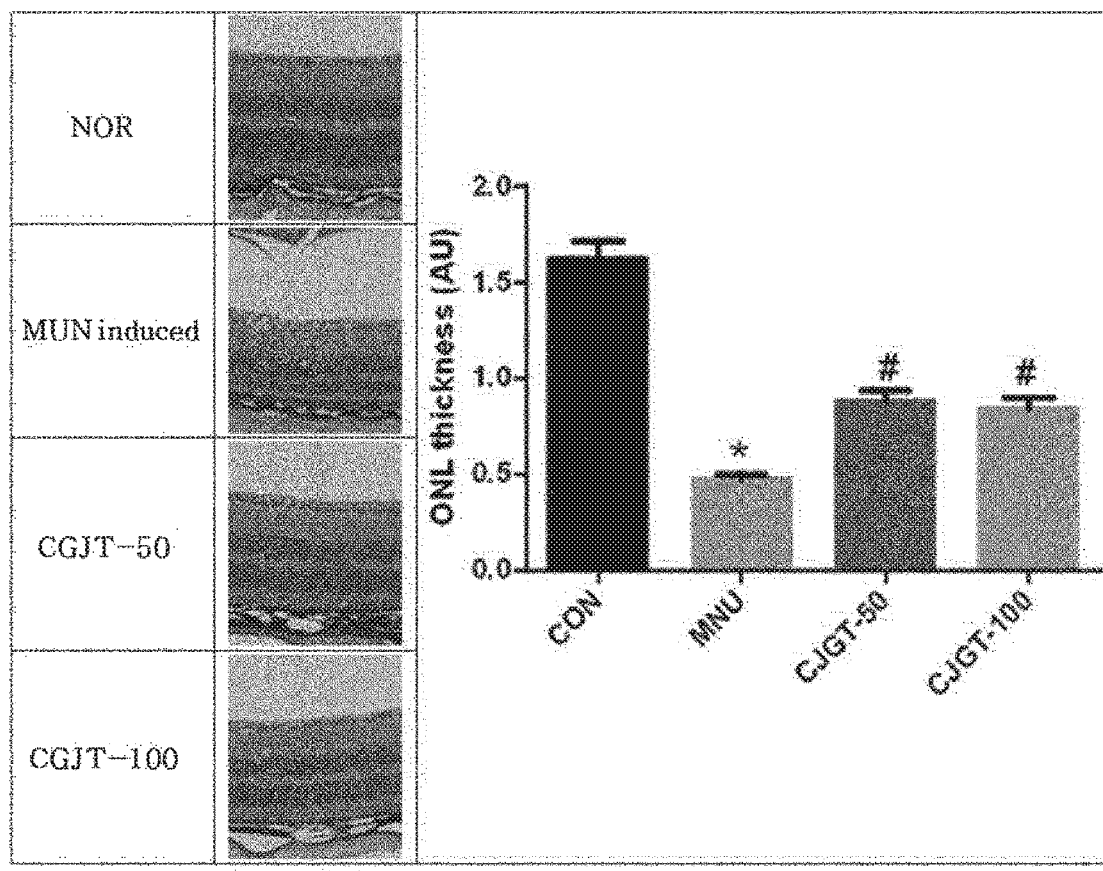
FIG. 5 is a diagram determining a preventive effect of macular degeneration through damage prevention of photoreceptor cells in MNU (N-methyl-N-nitrosourea)-induced macular degeneration animal models.

As in retinal section pictures of FIG. 5, it was confirmed that the thickness of outer nuclear layer compacted with nuclei of photoreceptor cells became thin, as the number of cells was reduced due to damage by MNU administration. However, it was confirmed that CJG50 and CJG100 of test drugs inhibited (treated) induction of macular degeneration by significantly inhibiting damage of photoreceptor cells by MNU (#p<0.05 vs MNU: FIG. 5).

<Experimental Example 7> Preventive Effect on Retinal Pigment Epithelial Cell Damage in NaIO$_3$-Induced Animal Models <7-1> Laboratory Animal Breeding and Experimental Design The 6-week-old male SD rats were used after acclimatization for 1 week. To induce damage and degeneration of retinal pigment epithelial cells as one of morphological changes of retinal tissues appearing in macular degeneration, 3.5% NaIO$_3$ (Sigma, USA) was injected into a sublingual vein of the 7-week-old rats (35 mg/kg). The same amount of physiological saline only was administrated to the normal group and the NaIO$_3$-induced group. Test drugs (CJG30R, CJGT) were suspended and compounded in 0.5% sodium carboxymethyl cellulose (CMC), orally administrated once in a concentration of 50 mg/kg and 100 mg/kg one day before NaIO$_3$ administration, and also orally administrated once per day for 7 days after NaIO$_3$ administration.

The same amount of 0.5% CMC was orally administered to the normal group and the control group.

Eyes were enucleated by carrying out an autopsy on the rats, and then mounted on 10% neutralized formalin and embedded in paraffin to prepare slide sections. Slide sections were stained with Hematoxylin & Eosin (H & E) and observed and evaluated about the folding number of outer nuclear layer of retinal tissues under an optical microscope.

<7-2> Experimental Results

The pigment epithelial cells were damaged due to NaIO$_3$ administration, so that a phenomenon was visually observed, which bends the outer nuclear layer compacted with nuclei of photoreceptor cells located just above them, the pigment epithelial cells. However, CJG30R-50, CJG30R-100, CJGT-50, and CJGT-100 of test drugs all inhibited damage of pigment epithelial cells induced by NaIO$_3$ and thus significantly inhibited the phenomenon bending the outer nuclear layer (FIG. 6).

<Experimental Example 8> Therapeutic Effect on Macular Degeneration in VLDLR (Very-Low-Density Lipoprotein Receptor) Knockout Mice <8-1> Laboratory Animal Breeding and Experimental Design A brace of Vldlr$^{-/-}$ mice, which are model animals showing subretinal neovasuclarization as a clinical sign of wet macular degeneration, were purchased from Jackson laboratory, and bred to obtain 2-week-old young mice, which were used in the experiment. As normal animals the same week-old C57BL/6 mice were used. The test drug (CJG30R) was suspended and compounded in 0.5% sodium carboxymethyl cellulose (CMC), and orally administered once per day in a concentration of 100 mg/kg for 7 days. In the normal group and the control group the same amount of 0.5% CMC only was orally administered.

<8-2> Measurement of Swelling in Retinal Blood Vessels

On an autopsy, the mice were anesthetized by mixing Zoletil 50 (Virbac 30 mg/kg) and Rompun (Bayer Korea, 10 mg/kg) in a ratio of 3:2 and diluting the mixture 10 times (saline), and then intraperitoneally injecting 50 μl. After cutting the abdomen open, 100 μl of the solution that 5 mg of fluorescein isothiocyanate-dextran (FD40S-1G, sigma) is dissolved in PBS was injected into the heart, and after 5 minutes eyes were enucleated, where one eye was mounted on 10% neutralized formalin for manufacturing retinal tissue sections and the other eye was mounted on 4% para-formaldehyde for 10 minutes, from which the retina was separated to manufacture flat-mounted retinal slides, with being observed under a fluorescent microscope (BX51, Olympus, Japan).

<8-3> Staining and Observation

After separating the retina from the eye tissues enucleated on the autopsy, the conjunctival tissues were mounted on 4% para-formaldehyde for 3 hours, washed with PBS and stirred in PBS containing 5% Triton X-100 and 1% BSA for 3 hours. After washing them again, they were incubated overnight at 4° C. with lectin (L2140, sigma) dissolved by 1 mg/ml in PBS to be diluted in 1:50. After washing them with PBS containing 0.05% Tween 20 for 2 hours, they were reacted with streptavidin TRITC to be diluted in 1:500 at 37° C. for 4 hours, washed with PBS for 30 minutes and observed with a fluorescent microscope (BX51, Olympus, Japan).

<8-4> Histopathological Evaluation

The eye mounted on 10% neutralized formalin on the autopsy for one day was embedded in paraffin to manufacture slide sections. The slide sections were stained with Hematoxylin & Eosin (H & E) and quantitatively analyzed about neovascularization lesions of the subretinal site under an optical microscope.

<8-5> Experimental Results (1) Inhibitory Effect on Retinal Blood Vessel Damage in Vldlr$^{-/-}$ Mice The phenomenon inhibiting retinal capillary damage was confirmed using retinal tissue sections, and consequently, the fluorescent materials were largely effused from the retinal blood vessels in the Vldlr$^{-/-}$ mice. However, such a phenomenon damaging retinal blood vessels was significantly inhibited by the CJG30R administration (FIG. 7).

(2) Inhibitory Effect on Subretinal Neovascularization

The neovascularization phenomenon in the subretinal sites appearing in the macular degeneration was confirmed using retinal tissue sections, and consequently, in the Vldlr$^{-/-}$ mice, the phenomenon was observed, which bend upward the retinal tissues by generating neovascular vessels in subretinal sites below the outer nuclear layer. However such angiogenesis was significant inhibited by the CJG30R administration (FIG. 8).

(3) Inhibitory Effect on Retinal Pigment Epithelial Cell Damage

To evaluate the integrity of retinal pigment epithelial cells, it was evaluated whether the morphological structure of cells was modified. The retinal pigment epithelial cells of normal mice were stained with ZO-1 and observed as an evenly aligned form, whereas in the Vldlr$^{-/-}$ mice cells were damaged and neovascular vessels were grown, so that a number of the modified sites (arrows) were observed. However, degeneration of the retinal pigment epithelial cells was significantly inhibited by administration of CJG30R (FIG. 9).

(4) Determination Inhibitory Effect on VEGF Expression in Retina

The slide sections were manufactured in the same manner as Experimental Example <8-4> above using animal models of Experimental Example <8-1> above. The slide sections were stained with H & E and quantitatively analyzed about the neovascularization lesions of the subretinal sites under an optical microscope.

As a result, as shown in FIG. 10, by observing the fact that VEGF as an important factor involved in permeability of neovascular vessels and blood vessels was severely expressed in the Vldlr$^{-/-}$ mice (stained in dark purple), whereas the expression was outstandingly inhibited by administrating CJG30R of the present invention, it was confirmed that the CJG30FR of the present invention exhibited the inhibitory effect of VEGF expression in the retina (FIG. 10).

\<Experimental Example 9\> Inhibitory Effect of CJG30R on Neovascularization in Laser-Induced Choroidal Neovascularization Rat Model

\<9-1\> Laboratory Animal Breeding and Experimental Design 7-week-old male Long-Evans rats (SLC Japan, Tokyo, Japan) were anesthetized by intraperitoneally injecting Zoletil 50 (Virbac 30 mg/kg) and Rompun (Bayer Korea, 10 mg/kg). Then, the pupil was expanded with 1% tropicamide eye drop, and photocoagulated spots were formed at four positions around optic nerve heads using a diode laser (wavelength: 532 nm, diameter: 100 μm, power: 150 mW, duration: 0.1 sec). Destruction of Bruch's membrane was verified by formation of characteristic bubbles. The rats recovered from anesthesia were randomly divided into groups to administrate drugs. Test drugs were suspended and compounded in 0.5% sodium carboxymethyl cellulose (CMC), and orally administrated in a concentration of 100 mg/kg once per day for 10 days. In the control group the same amount of 0.5% CMC only was orally administered.

\<9-2\> Evaluation of Choroidal Neovascularization

After 10 days, the rats were anesthetized by intraperitoneally injecting a mixed solution of Zoletil 50 (Virbac 30 mg/kg) and Rompun (Bayer Korea, 10 mg/kg) in a ratio of 3:2 on an autopsy. After cutting the abdomen open, 100 μl of the solution that 5 mg of fluorescein isothiocyanate-dextran (MW $2\times10^6$, sigma) is dissolved in PBS was injected into the heart, and after 10 minutes eyes were enucleated and mounted on 4% para-formaldehyde for 10 minutes, from which the retina was separated, and the conjunctival tissues containing subretinal sites were manufactured into flat-mounted slides, with being observed under a fluorescent microscope (BX51, Olympus, Japan). The size of neovascularization sites was analyzed using Image J software (NIH, USA).

\<9-3\> Inhibitory Effect on Subretinal Neovascularization

The phenomenon of neovascularization in subretinal sites appearing in the macular degeneration was confirmed using the retinal tissue sections, and consequently CJG30R showed a tendency to inhibit the neovascularization (FIG. 11).

\<Experimental Example 10\> Comparative Experiment of Preventive and Therapeutic Effect of CJG30R Paeoniflorin (PF) in MNU-Induced Age-Related Macular Degeneration Models It has been reported that since paeoniflorin (PF) has inhibitory effects on the cell death due to $H_2O_2$ and the oxidative stress in human retinal pigment epithelial cell lines (ARPE-19), it will be effective in eye diseases such as macular degeneration (Molecular Vision 2011; 17: 3512-3522). However, it was not verified whether it had the preventive and therapeutic effect of macular degeneration in animal models, although the antioxidant effect and the cell death inhibition were merely confirmed after adding $H_2O_2$ as a toxic material, instead of in an aging condition, as a general cause of macular degeneration, in only retinal pigment epithelial cell lines, and thus it was not verified in the animal models for demonstrating whether it has truly the effect on macular degeneration.

Accordingly, although paeoniflorin was contained in the materials invented by the present inventors, for verifying the fact that the present materials do not have only a single effect of paeoniflorin, an experiment was carried out about paeoniflorin (PF-6.5) having the content contained in 100 mg of CJG30R, and CJG30R (100 mg) as follows.

\<10-1\> Laboratory Animal Breeding and Experimental Design

The 6-week-old male C57BL/6 mice were used after acclimatization for 1 week. To induce damage and degeneration of photoreceptor cells among morphological changes of retinal tissues appearing in macular degeneration, 1% (0.05% acetic acid) N-methyl-N-nitrosourea (MNU, Sigma, USA) was intraperitoneally injected to the 7-week-old male C57BL/6 mice (60 mg/kg). The same amount of 0.05% acetic acid was intraperitoneally administered to the normal group. CJG30R (100 mg/kg) and PF-6.6 (6.5 mg/kg) as test drugs were suspended and compounded in 0.5% sodium carboxymethyl cellulose (CMC), orally administrated one day before MNU administration, and orally administrated once per day for 7 days after MNU administration. The same amount of 0.5% CMC was orally administrated to the normal group and the MNU-induced group.

\<10-2\> Histopathological Evaluation

After completing administration of the test drugs, eyes were enucleated by carrying out an autopsy on the mice, and then mounted on 10% neutralized formalin for one day and embedded in paraffin to prepare slide sections. Slide sections were stained with Hematoxylin & Eosin (H & E) and observed under an optical microscope. The damage and degeneration of the photoreceptor cells were measured and evaluated by thickness changes in the outer nuclear layer of the retinal tissues.

\<10-3\> Experimental Results

The significant effect in the CJG30R administration group was verified as compared to the MNU administration group, but the administration group (PF-6.5) having the content of paeoniflorin contained in 100 mg of CJG30R had no effect at all (Table 4 and FIG. 12).

That is, as in retinal section pictures of FIG. 11, in the damage degree of the outer nuclear layer compacted with nuclei of photoreceptor cells in the retina, the MNU administration group was deteriorated by almost 50% or more ($1.99\pm0.21 \rightarrow 0.92\pm0.17$ AU: * $p<0.05$ vs NOR). But in the CJG30R administration group the effect was improved by 35% as compared to the MNU administration group ($0.92\pm0.17$ AU $\rightarrow 1.19\pm0.29$ AU: # $p<0.05$ vs MNU), although paeoniflorin (PF-6.5), a single compound itself, had no effect at all (see Table 4 and FIG. 11).

TABLE 4

Inhibitory effect of CJG30R on outer nuclear layer (ONL) damage in MNU-induced animal models

| Group | ONL thickness (AU) | ONL thickness (%) |
|---|---|---|
| NOR | 1.99 ± 0.21 | 100.00 ± 27.72 |
| MNU | 0.92 ± 0.17* | 0.00 ± 25.55* |

TABLE 4-continued

Inhibitory effect of CJG30R on outer nuclear layer
(ONL) damage in MNU-induced animal models

| Group | ONL thickness (AU) | ONL thickness (%) |
|---|---|---|
| CJG30R | 1.19 ± 0.29# | 35.27 ± 14.86# |
| PF-6.5 | 0.96 ± 0.17 | 3.52 ± 16.11 |

(*p < 0.05 vs NOR; #p < 0.05 vs MNU)

Although CJG30R and CJGT contained paeoniflorin (PF) in a content of 6.5% and 6.1%, respectively, it was verified that the effects of CJG30R and CJGT were not due to only a single compound of paeoniflorin, but a synergistic effect of numerous single components present in CJG30R and CJGT.

INDUSTRIAL APPLICABILITY

The invention can be not only pharmaceutically available as a natural extract composition effective in preventing and treating angioedema, but also usefully utilized as a health functional food.

What is claimed is:

1. A method for treating angioedema, comprising administrating a pharmaceutically effective amount of a mixed extract consisting of peony root and licorice as active ingredients, and a pharmaceutically acceptable additive to a subject suffering from angioedema, wherein the angioedema is selected from the group consisting of macular degeneration, macular edema and retinal edema.

2. The method for treating angioedema according to claim 1, wherein the mixed extract is obtained by extracting peony root and licorice with water, ethanol or methanol, or a mixture thereof as a solvent.

3. The method for treating angioedema according to claim 1, wherein the mixed extract is obtained by extracting peony root and licorice by a process selected from the group consisting of reduced pressure and high temperature extraction, boiling water extraction, reflux extraction, hot water extraction, cold extraction, normal temperature extraction, ultrasonic extraction or vapor extraction.

4. The method for treating angioedema according to claim 1, wherein said peony root and said licorice are in a weight ratio of 10:1 to 1:1, respectively.

5. The method for treating angioedema according to claim 1, wherein said peony root and said licorice are in a weight ratio of 2:1, respectively.

6. The method for treating angioedema according to claim 1, wherein said mixed extract inhibits abnormal generation of advanced glycation end products (AGEs).

7. The method for treating angioedema according to claim 1, wherein said mixed extract breaks cross-linking of advanced glycation end products with matrix proteins.

8. A method for ameliorating angioedema, comprising administrating a physiologically effective amount of a mixed extract consisting of peony root and licorice to a subject suffering from angioedema.

9. The method for ameliorating angioedema according to claim 8, wherein the mixed extract is obtained by extracting peony root and licorice with water, ethanol or methanol, or a mixture thereof as a solvent.

10. The method for ameliorating angioedema according to claim 8, wherein the mixed extract is obtained by extracting peony root and licorice by a process selected from the group consisting of reduced pressure and high temperature extraction, boiling water extraction, reflux extraction, hot water extraction, cold extraction, normal temperature extraction, ultrasonic extraction or vapor extraction.

11. The method for ameliorating angioedema according to claim 8, wherein said peony root and said licorice are in a weight ratio of 10:1 to 1:1, respectively.

12. The method for ameliorating angioedema according to claim 8, wherein said peony root and said licorice are in a weight ratio of 2:1, respectively.

13. The method for ameliorating angioedema according to claim 8, wherein said mixed extract inhibits abnormal generation of advanced glycation end products (AGES).

14. The method for ameliorating angioedema according to claim 8, wherein said mixed extract breaks cross-linking of advanced glycation end products with matrix proteins.

* * * * *